United States Patent
Figueroa et al.

(10) Patent No.: US 7,727,576 B2
(45) Date of Patent: Jun. 1, 2010

(54) SYSTEM AND A METHOD FOR PRODUCING LAYERED ORAL DOSAGE FORMS

(75) Inventors: Iddys D. Figueroa, Dorado, PR (US); Orlando Ruiz, Aguadilla, PR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 750 days.

(21) Appl. No.: 10/825,870

(22) Filed: Apr. 16, 2004

(65) Prior Publication Data

US 2005/0233000 A1    Oct. 20, 2005

(51) Int. Cl.
*B05D 3/02* (2006.01)
*A61K 9/28* (2006.01)
*A61K 9/48* (2006.01)
*A61J 3/06* (2006.01)

(52) U.S. Cl. .................. 427/2.14; 427/2.1; 427/2.21; 427/2.22; 424/452; 424/464; 424/489; 424/490

(58) Field of Classification Search .................. 417/2.1, 417/2.21, 469; 428/303.4; 424/400; 118/664
See application file for complete search history.

(56) References Cited

U.S. PATENT DOCUMENTS

| | | | |
|---|---|---|---|
| 4,197,289 A | 4/1980 | Lipinsky et al. | |
| 4,865,851 A * | 9/1989 | James et al. | 424/498 |
| 6,555,175 B2 | 4/2003 | Johnson | |
| 6,599,627 B2 | 7/2003 | Yeo et al. | |
| 6,602,511 B2 * | 8/2003 | von Corswant | 424/400 |
| 6,962,715 B2 * | 11/2005 | Lee et al. | 424/439 |
| 7,153,538 B2 * | 12/2006 | Brown et al. | 427/2.14 |
| 2002/0127014 A1 * | 9/2002 | Wallace | 396/564 |
| 2002/0197388 A1 * | 12/2002 | Brown et al. | 427/2.1 |
| 2003/0059471 A1 * | 3/2003 | Compton et al. | 424/489 |
| 2003/0065294 A1 * | 4/2003 | Pickup et al. | 604/304 |
| 2004/0173146 A1 * | 9/2004 | Figueroa et al. | 118/325 |

FOREIGN PATENT DOCUMENTS

| | | | |
|---|---|---|---|
| DE | 217989 A * | 1/1985 | |
| WO | WO 01/34121 A2 | 5/2001 | |
| WO | WO 03/028797 A | 4/2003 | |

* cited by examiner

Primary Examiner—Timothy H Meeks
Assistant Examiner—Cachet I Sellman (57) ABSTRACT

A method for producing an oral medication includes dispensing a structural material, the structural material including one of a polymer or a gelatin, curing the structural material, and dispensing a jettable pharmaceutical solution onto the cured structural material.

45 Claims, 6 Drawing Sheets

SYSTEM AND A METHOD FOR PRODUCING LAYERED ORAL DOSAGE FORMS

BACKGROUND

Traditional oral dosage drug formulations include both active pharmaceutical ingredients (API) and inactive ingredients. The inactive ingredients (also called excipients), are components of the final formulation of a drug that are not considered active pharmaceutical ingredients (API) in that they do not directly affect the consumer in the desired medicinal manner. Traditional oral dosage forms have several inactive ingredients. Among the traditional inactive ingredients included in oral dosage forms are binders that hold the tablet together, coatings configured to mask an unpleasant taste, disintegrants configured to make the tablet break apart when consumed, enteric coatings, fillers that assure sufficient material is available to properly fill a dosage form, enhancers configured to increase stability of the active ingredients, preservatives aimed at preventing microbial growth, and the like.

The above-mentioned inactive ingredients have also been used to develop controlled release oral dosage solid formulations. These controlled release oral dosage solid formulations are designed to temporally control the release of the API from the oral dosage drug formulation. This temporal control allows for a time delayed release, or an extended release of a desired API formulation. The selection and optimization of the inactive ingredients to obtain an oral dosage solid form with the desired controlled release properties is both a complex and a lengthy process.

In addition to the complexity and difficulty traditionally associated with selecting and optimizing inactive ingredients to obtain an oral dosage solid form with controlled release properties, there are a number of relatively insoluble drugs that are not well suited to sustained or controlled delivery. The formulation of these low water soluble or insoluble APIs into controlled or modified-release dosage forms using traditional formulation methods is both expensive and challenging due to the API's solubility properties.

SUMMARY

A method for producing an oral medication includes dispensing a structural material, the structural material including one of a polymer or a gelatin, curing the structural material, and dispensing a jettable pharmaceutical solution onto the cured structural material.

BRIEF DESCRIPTION OF THE DRAWINGS

The accompanying drawings illustrate various embodiments of the present system and method and are a part of the specification. The illustrated embodiments are merely examples of the present system and method and do not limit the scope thereof.

Throughout the drawings, identical reference numbers designate similar, but not necessarily identical, elements.

DETAILED DESCRIPTION

A number of exemplary systems and methods for producing a layered polymer or gelatin based oral dosage form are disclosed herein. More specifically, a jettable pharmaceutical solution is jetted onto an edible polymer or gelatin based structure to form an oral dosage form. The jettable pharmaceutical solution may include any number of solvents to further modify the release rate of an oral drug formulation.

As used in the present specification and the appended claim, the term "edible" is meant to be understood broadly as any composition that is suitable for human consumption and is non-toxic. Similarly, the phrase "suitable for human consumption" is meant to be understood as any substance that complies with applicable standards such as food, drug, and cosmetic (FD&C) regulations in the United States and/or Eurocontrol experimental centre (E.E.C.) standards in the European Union. Additionally, the term "ink" is meant to be understood broadly as meaning any jettable fluid configured to be selectively emitted from an inkjet dispenser, regardless of whether it contains dye or any other colorant. The term "jettable" is meant to be understood both in the present specification and in the appended claims as any material that may be selectively deposited by any digitally addressable inkjet material dispenser. Also, the term "gelatin" is meant to be understood generally as referring to any edible thickening agent, which when dissolved in hot water and then cooled, forms a solid.

In the following description, for purposes of explanation, numerous specific details are set forth in order to provide a thorough understanding of the present system and method for producing a layered polymer or gelatin oral dosage form. It will be apparent, however, to one skilled in the art, that the present method may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Exemplary Structure

Figure 1:
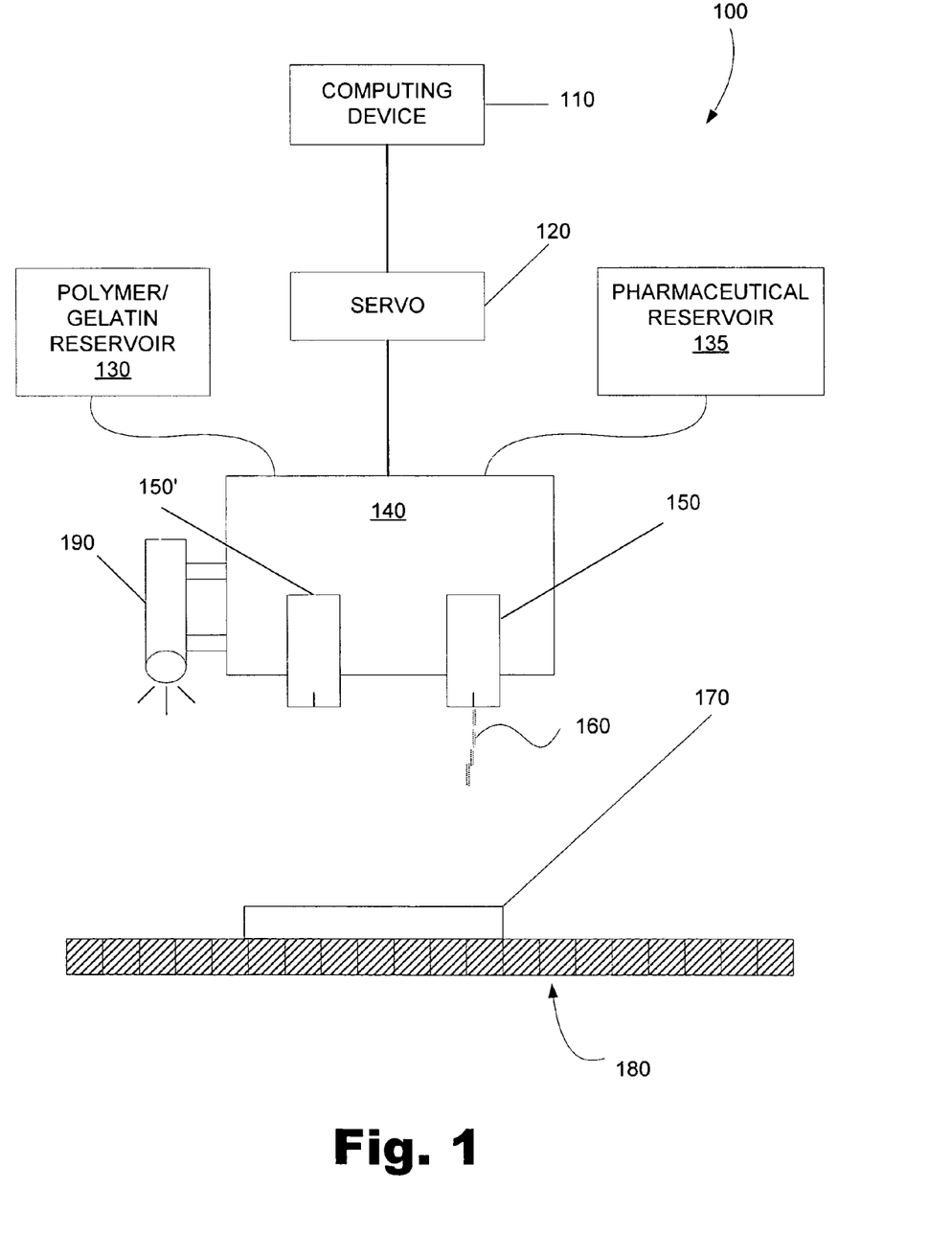
FIG. 1 is a simple block diagram illustrating a system that may be used to form a layered polymer/gelatin oral dose, according to one exemplary embodiment.

FIG. 1 illustrates an exemplary formulation system (100) that may be used to apply a jettable pharmaceutical solution (160) to an edible structure (170) according to one exemplary embodiment. As shown in FIG. 1, the present system includes a computing device (110) controllably coupled through a servo mechanism (120) to a moveable carriage (140) having a plurality of inkjet dispensers (150, 150') disposed thereon. A structural material reservoir (130) is coupled to a first inkjet material dispenser (150') while a jettable pharmaceutical reservoir (135) is fluidly coupled to a second inkjet material dispenser (150). A substrate (180) is located adjacent to the inkjet dispenser (150) having an edible structure (170) disposed thereon. The edible structure (170) is configured to receive a jettable pharmaceutical solution (160). Additionally, according to the exemplary embodiment illustrated in FIG. 1, a thermal energy source (190) is coupled to the moveable carriage (140). The above-mentioned components of the present formulation system (100) will now be described in further detail below.

The computing device (110) that is controllably coupled to the servo mechanism (120), as shown in FIG. 1, controls the selective deposition of both a structural material used to form the edible structure (170) as well as a jettable pharmaceutical solution (160). According to one exemplary embodiment, a representation of the edible structure (170) or a desired quantity or dosage of the jettable pharmaceutical solution (160) may be generated on an application hosted by the computing device (110). The generated representation may then be converted into servo instructions that are housed in a processor readable media (not shown). When accessed by the computing device (110), the instructions housed in the processor readable media are used to control the servo mechanisms (120) as well as the movable carriage (140) and inkjet dispensers (150), causing them to selectively deposit the above-mentioned materials. The computing device (110) illustrated in FIG. 1 may be, but is in no way limited to, a workstation, a personal computer, a laptop, a personal digital assistant (PDA), or any other processor containing device.

The moveable carriage (140) of the present formulation system (100) illustrated in FIG. 1 is a moveable material dispenser that may include any number of inkjet material dispensers (150, 150') configured to dispense the present jettable pharmaceutical solution (160) and/or the structural material housed in the polymer/gelatin reservoir (130). The moveable carriage (140) may be controlled by a computing device (110) and may be controllably moved by, for example, a shaft system, a belt system, a chain system, etc. making up the servo mechanism (120). As the moveable carriage (140) operates, the computing device (110) may inform a user of operating conditions as well as provide the user with a user interface.

As a desired quantity of the jettable pharmaceutical solution (160) or the structural material is printed, the computing device (110) may controllably position the moveable carriage (140) and direct one or more of the inkjet dispensers (150, 150') to selectively dispense a desired material at predetermined locations as digitally addressed drops. The inkjet material dispensers (150, 150') used by the present formulation system (100) may be any type of inkjet dispenser configured to perform the present method including, but in no way limited to, thermally actuated inkjet dispensers, mechanically actuated inkjet dispensers, electro-statically actuated inkjet dispensers, magnetically actuated dispensers, piezo-electrically actuated inkjet dispensers, continuous inkjet dispensers, etc. Additionally, the ink-jet material dispenser can be heated to assist in dispensing the above mentioned solutions. Moreover, the present structural material used to form the edible structure (170) can be distributed using any number of printing processes including, but in no way limited to, inkjet printing, lithography, screen printing, gravure, and flexo printing.

The polymer/gelatin reservoir (130) that is fluidly coupled to the first inkjet material dispenser (150') houses a material used to form the edible structure (170) prior to printing. Similarly, the pharmaceutical solution reservoir (135) that is fluidly coupled to one of the inkjet material dispensers (150) houses the pharmaceutical solution (120) prior to printing. The material reservoirs may be any sterilizeable container configured to hermetically seal the above-mentioned materials prior to printing and may be constructed of any number of materials including, but in no way limited to metals, plastics, composites, ceramics, or appropriate combinations thereof.

FIG. 1 also illustrates the components of the present system that facilitate reception of the jettable pharmaceutical solution (160) and the deposited edible structure (170). As shown in FIG. 1, a substrate (180) may receive and/or positionally secure an edible structure (170) during a printing operation. The formation and composition of the jettable pharmaceutical solution (160) and the edible structure (170) will now be described in detail below.

Exemplary Composition

Figure 2:
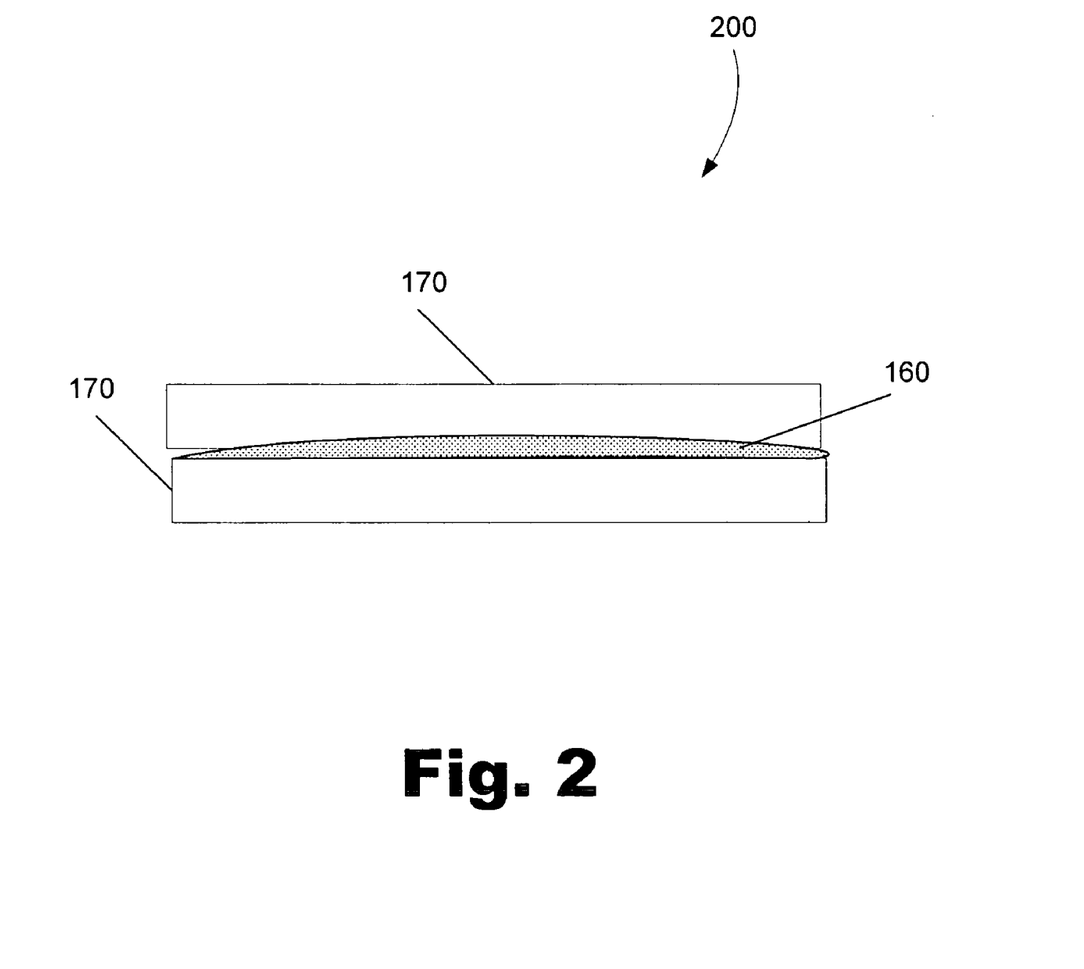
FIG. 2 is a perspective view of a layered polymer/gelatin oral dose, according to one exemplary embodiment.

According to one exemplary embodiment, the present system and method may be performed by selectively depositing a jettable pharmaceutical solution (160) onto any number of layers of an edible structure (170). Accordingly, a number of edible structures (170) may be used to receive the jettable pharmaceutical solution (160). FIG. 2 illustrates a layered oral dosage (200) formed by the formulation system (100; FIG. 1) illustrated in FIG. 1, according to one exemplary embodiment. As illustrated in FIG. 2, the layered oral dosage (200) includes a jettable pharmaceutical solution (160) disposed onto an edible structure (170). As shown in FIG. 2, the edible structure (170) replaces the use of traditional powders as inactive ingredients in the oral dosage (200) solid form. Consequently, the edible structure (170) can be used in combination with inkjet technology to produce a layered solid oral dosage form of a pharmaceutical without the traditionally complex and costly manufacturing processes. Moreover, the present edible structure (170) may be precisely formed using inkjet technology as will be explained in further detail below.

According to one exemplary embodiment, an edible structure (170) is formed prior to the dispensing of any jettable pharmaceutical solutions (160). According to this exemplary embodiment, one or more edible structures (170) is formed by selectively dispensing a solution of an edible polymer or gelatin based material onto a substrate (180; FIG. 1) and curing or otherwise solidifying the edible structure or structures. Accordingly, the edible structure may be made out of, but is in no way limited to, maltotriose-based pullulan, gelatin, polyvinyl alcohol (PVA), PVA-polyethylene oxide, PVA-vinylamine, polyvinyl pyrrolidone (PVP), PVP-polyvinyl acetate, cationic PVP, crosslinked PVP, sorbitol, wheat gluten, seaweed, cellulose, methyl cellulose, hydroxypropyl methyl cellulose (HPMC), poly vinyl methyl ether (PVME), PVME-propylene glycol monomethyl ether acetate (PMA), poly(2-ethyl 2-oxazoline), and/or pectin. Similarly, the substrate (180; FIG. 1) receiving the edible structure can be an inert non-adhesive material such as Teflon or glass from which a completed layered oral dosage (200) can be peeled. Alternatively, the substrate (180; FIG. 1) can be a sheet of a fast dissolving, water-soluble edible polymer such as pullulan, polyvinyl alcohol (PVA), polyvinyl pyrrolidone (PVP), calcium alginate, gelatin, or an appropriate combination thereof which may be readily consumed with the resulting layered oral dosage.

According to one exemplary embodiment of the present system and method, the above-mentioned edible structure (170), once cured or otherwise solidified, receives a jettable pharmaceutical solution (160; FIG. 1) thereby forming a layered oral dosage of a pharmaceutical product. The jettable pharmaceutical solution (160) illustrated in FIG. 1 that is selectively deposited onto the edible structure (170) may include both an oral drug component and a jettable vehicle component, as illustrated below.

The oral drug component of the jettable pharmaceutical solution (160) includes the desired API that forms a desired drug dosage. While the present system and method is exceptionally suited for traditionally insoluble oral drug components, any number of oral drug components may be incorporated by the present exemplary system and method including, but in no way limited to, Prednisolone, Glyburide, Lovastatin, Digoxin, and/or Nifedipine. Additionally, according to one exemplary embodiment, the oral drug component of the jettable pharmaceutical solution (160) may include, but is in no way limited to, ace inhibitors, antianxiety medications, antibiotics, antihypertensive medications, antiviral medications, blood glucose regulators, Alzheimer-type dementia medications, anorexiants/central nervous system (CNS) stimulants, antidiuretics, specific antidotes, antihistamines, antipsychotic/antimanic medications, beta blockers, calcium channel blockers, contraceptives, dermatologics, diuretics, estrogens/progestins, entrapyramidal movement disorders (and hyperprolactinemia), and sedatives/hypnotics.

Examples of the above mentioned oral drug components of the jettable pharmaceutical solution (160) include, but are in no way limited to, triazolam, felodipine, trandolapril, pergolide, rivastigmine tartrate, sibutramine hydrochloride, desmopressin acetate, flumazenil, desloratadine, risperidone, carvedilol, isradipine, norgestimate, methoxsalen, metolazone, estradiol, estrogens, conjugated estrogent, esterified cabergoline, zaleplon, and zolpidem tartrate.

In addition to the above-mentioned oral drug component, the present jettable pharmaceutical solution (160; FIG. 1) includes a jettable vehicle component configured to provide properties to the oral drug formulation enabling the deposition of the oral drug formulation from an inkjet dispensing device. According to one exemplary embodiment, the jettable vehicle component of the jettable pharmaceutical solution (160; FIG. 1) includes, but is in no way limited to, an edible solvent, surfactants, and/or humectants. Solvents and/or surfactants may be added to the jettable pharmaceutical solution (160) to enhance the jettable properties of the jettable oral drug formulation and to interact with the surface of the edible structure (170). Additional additives such as humectants can also be added to the jettable oral drug formulation to improve the reliability of an associated inkjet dispenser by reducing the likelihood of clogged nozzles.

According to one exemplary embodiment of the present system and method, the edible solvent component of the present jettable vehicle is configured to disperse and transport the oral drug component, and any other additives, of the present jettable pharmaceutical solution (160). The vehicle solvent component imparts a jettable viscosity to the jettable pharmaceutical solution (160) while also evaporating at a rate sufficient to make a desired dosage resistant to contact soon after it is deposited on an edible structure (170). According to one exemplary embodiment, the solvent is either a suitable organic solvent that does not dissolve the edible structure (170) or an edible solvent that slightly dissolves the edible structure. Selection of an appropriate solvent component is dependant upon a relationship between the solvent component and the edible structure (170) employed. Table 1 below illustrates a number of exemplary edible solvent components and exemplary preparation temperatures that may be selected based on the polymer employed.

TABLE 1

| Exemplary Edible Structure | Exemplary Dissolving Solvent | Exemplary Non-Dissolving Solvents |
|---|---|---|
| Pullulan (maltotriose-based) | Water, Methanol Acetonitrile at 298 K acetone/DMSO (43.5/56.5) at 293 K DMSO/methanol (49/51) at 298 DMSO/0.5 mol/L KCl in water (25/75) at 298 K KCl/water (0.33 mol/L) at 295.5 K | Organic solvents |
| Gelatin | Water at 298 K | Organic solvents |
| PVA (polyvinyl alcohol) | t-butanol/water (32/68 w/w) at 298 K | Hydrocarbons |
| | Ethanol/water (41.5/58.5 w/w) at 298 K | Chlorinated HCs |
| | Methanol/water (41.7/58.3 w/w) at 298 K | Lower alcohols |
| | l-propanol/water (39.4/60.6 w/w) at 298 K | THF |
| | n-propanol/water (35.1/64.9 w/w) at 298 K | Ketones |
| | NaCl/water (2 mol/L) at 298 K Water at 370 K Piperazine Diethylene-diamine Formamide DMF DMSO (hot) Water Hexamethylphosphoric triamide Glycols (hot) Glycerol (hot) | Carboxylic acids Esters Concentrated Aqueous salt solutions |
| PVP (polyvinyl pyrrolidone) | Water, polar solvents, dichloromethane | Organic solvents |
| PVP-polyvinyl acetate | Acetone/water (66.8/33.2 w/w) at 298 K | |
| PVP-polyvinyl acetate | Dioxane at 263 K | |
| PVP | NaCl/water (0.55 mol/L) at 298 K | |
| Sorbitol | Water at 298 K | Organic solvents |
| Seaweed | Same as for Pullulan, except for fiber portion | Organic Solvents |
| Methyl cellulose | Aqueous alkalis | Water (hot) |
| | Water (cold) | Methanol |
| | Methanol/methylene chloride | Diethyl ether |
| | N-ethylpyridinium chloride/DMF (1:1) | Methylene chloride |
| | Chloroform | Ethanol |
| | Acetone | Aliphatic hydrocarbons |
| | Pyridine | Diluted Aqueous alkalis |
| | Esters Cyclohexanone N-ethylpyridinium chloride/pyridine (1:1) | |
| Hydroxypropyl Methyl cellulose (HPMC) | Water (cold) | Organic solvents |
| Pectin | Water Diluted acids Ethylene diamine | Alcohol |

As illustrated in Table 1, the solvent component of the jettable pharmaceutical solution (160) may be either dissolving or non-dissolving of the edible structure (170). According to one exemplary embodiment, if a non-dissolving solvent component is incorporated into the jettable pharmaceutical solution (160) and is printed on top of the edible structure (170) in discretely addressed locations, a small particle size of jettable solution will remain on the surface of the edible structure. This embodiment is advantageous for low water-solubility drugs in that the present exemplary method produces a large surface area of jettable pharmaceutical solution. When consumed, this large surface area may be in simultaneous contact with a consuming material, thereby allowing for faster dissolution.

Alternatively, if a solvent component of the jettable pharmaceutical solution (160) is selected to slightly dissolve the edible structure (170), alternative characteristics will be manifest. According to this exemplary embodiment, as the slightly dissolving solvent component evaporates, the oral drug component is incorporated into the structural web of the edible structure. Variations of the degree of incorporation of the oral drug component into the structural web of the edible structure (170) may be achieved by varying the solvent component and quantity used. By repeating the deposition of jettable pharmaceutical solutions (160) having various combinations of solvent onto various edible structures (170), the resulting layered oral dosage may have different and customizable controlled-release characteristics.

Surfactants and emulsifiers may also be added to the solvent component of the present jettable pharmaceutical solution (160) in order to facilitate dispersion and/or dissolution of the oral drug component and any other additive in the solvent. Typically, an edible alcohol may be used as the vehicle surfactant including, but in no way limited to, ethyl alcohol, glycerol, methyl alcohol, isopropyl alcohol, and butyl alcohol. Ethyl alcohol, for example, decreases the surface tension of water, thereby allowing an oral drug component and other additives to dissolve and/or disperse throughout the water more easily. The ethyl alcohol may also facilitate the jettability of the present jettable pharmaceutical solution (160). Moreover, other edible compounds besides alcohols may also be used as the surfactant or emulsifier, including, but in no way limited to, lecithin, crillet, polyoxyethylene sorbitan monostearate (TWEEN), xanthan gum, sorbitol, and starches such as maize starch, corn starch, and potato starch.

A humectant may also be included in the present jettable pharmaceutical solution to control the moisture content and viscosity of the resulting jettable pharmaceutical solution (160). Premature drying decreases viscosity and thus may inhibit the jettability of the jettable pharmaceutical solution (160). Therefore, a humectant may be included in the vehicle to keep the jettable pharmaceutical solution (160) from premature drying. The humectant may include, but is in no way limited to glycerin, sorbitol, mannitol, or any other edible humectant.

According to one exemplary embodiment, the vehicle component of the present jettable pharmaceutical solution (160) may also include other additives as desired including, but in no way limited to, driers, thinners, waxes, lubricants, reducing oils and solvents, body gum, binding varnish, antioxidants, anti-skinning agents, resins, and/or binders.

Additionally, the present jettable pharmaceutical solution (160) may also include an edible colorant component according to one exemplary embodiment. Suitable colorants include any edible compounds, or combinations thereof, including, but in no way limited to, FD&C approved colorants. The afore-mentioned colorants may also be water-soluble, further facilitating their incorporation into a water-based oral drug formulation.

According to one exemplary embodiment, PVA, PVP, and pullulan solutions have been successfully fired from a thermal inkjet dispenser onto glass surface. The solutions fired were 5% (w/v) polymer in either 100% ethanol or water and 50% (v/v) ethanol/water solutions. Additionally, the solutions were fired over pullulan films and found that the water-based formulation dissolves the pullulan, while the 50% alcohol/water formulation does not dissolve the pullulan layer. Consequently, the alcohol/water concentrations can be deviated to vary the amount of dissolution thereby incorporating the jettable pharmaceutical solution into the polymer web.

Exemplary Implementation and Operation

Figure 3:
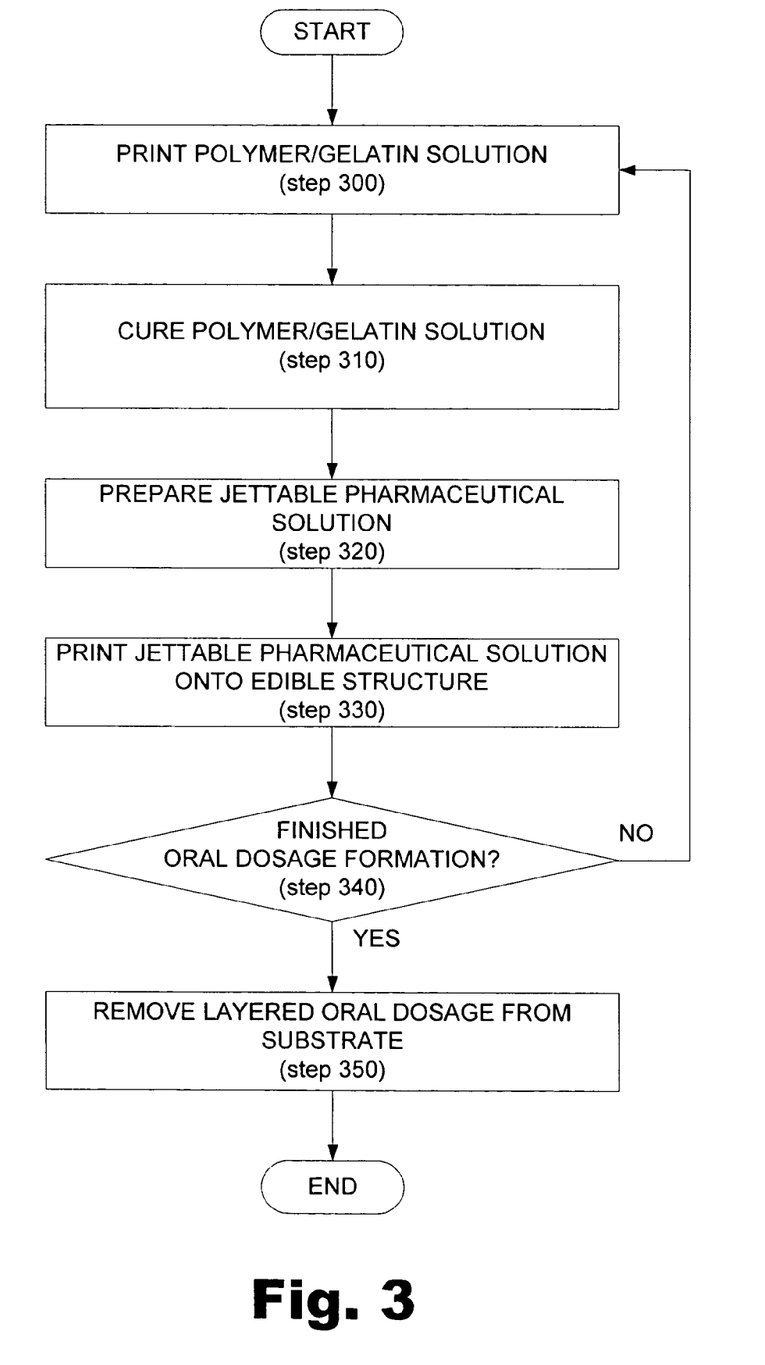
FIG. 3 is a flow chart illustrating a method for forming a layered polymer/gelatin oral dose, according to one exemplary embodiment.

FIG. 3 illustrates an exemplary method for forming a layered oral dosage according to one exemplary embodiment. As illustrated in FIG. 3, the present method begins by printing or otherwise depositing a polymer/gelatin solution onto a receptive substrate (step 300). After deposition of the polymer/gelatin solution onto a receptive substrate, the deposited polymer/gelatin solution is cured to form an edible solution receiving structure (step 310). With the edible solution forming structure formed, a jettable pharmaceutical solution may be prepared (step 320) and printed onto the edible solution receiving structure (step 330). After a desired amount of the jettable solution has been dispensed onto the edible solution receiving structure, the system may determine whether the oral dosage formation is complete (step 340). If the oral dosage formation is not yet complete (NO, step 340), another layer of polymer/gelatin solution is printed onto the previously formed edible structure (step 300) and the process is again performed. Once sufficient edible structures and jettable pharmaceutical solution layers have been formed to complete the oral dosage formation (YES, step 340), the layered oral dosage form may optionally be removed from the substrate (step 350). Further details of the above-mentioned method will be given below with reference to FIGS. 3 through 9.

Figure 4:
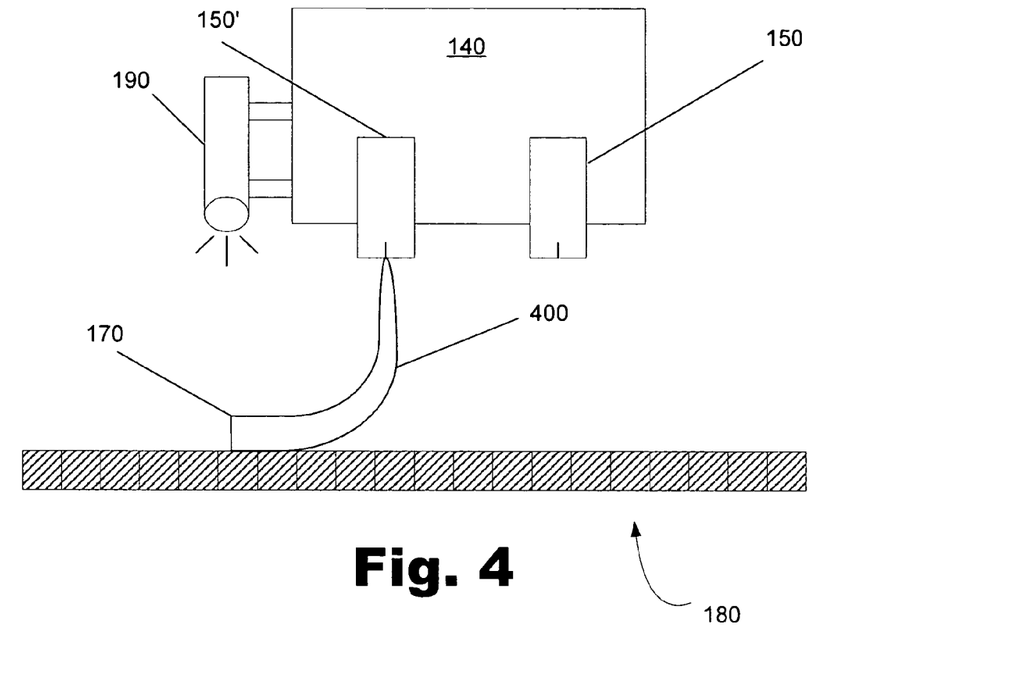
FIG. 4 is a simple magnified view of a pharmaceutical receiving edible structure, according to one exemplary embodiment.

As noted above, the present method is initiated by printing or otherwise depositing a polymer/gelatin solution onto a receptive substrate (step 300). FIG. 4 illustrates one exemplary method for depositing a polymer/gelatin solution onto a receptive substrate. As illustrated in FIG. 4, the polymer/gelatin solution (400) may be disposed onto a substrate (180) by an inkjet material dispenser (150) that is coupled to the moveable carriage (140). According to this exemplary embodiment, the polymer/gelatin solution (400) comprises a jettable viscosity that may be selectively deposited by the inkjet material dispenser (150) to form a film or edible structure (170) of a desired thickness. According to one exemplary embodiment, the printing of the polymer/gelatin solution onto a receptive substrate (step 300; FIG. 3) includes dispensing a plurality of independent quantities of the polymer/gelatin solution onto discrete locations of the substrate (180). As a result of forming independent structures, and utilizing precise inkjet material dispensers (150), each independent structure may selectively receive jetted pharmaceuticals in varying concentrations and formulations.

Also illustrated in FIG. 4, the polymer/gelatin solution (400) may be cured into an edible structure (170) upon deposition onto the substrate (step 310; FIG. 3). The polymer/gelatin solution (400) may be cured according to any number of material curing methods including, but in no way limited to, a vacuum drying process, or the application of thermal energy. As illustrated in FIG. 4, a thermal energy source (190) may be coupled to the moveable carriage (140) thereby providing a controllable curing device.

Once the polymer/gelatin solution (400) is cured to form an edible structure (170), a jettable pharmaceutical solution is prepared to be emitted onto the edible structure. As mentioned previously, the jettable pharmaceutical may include any number of APIs and solvents to allow for the design of resulting medicinal effects and temporal dosage release. According to one exemplary embodiment, a non-dissolving organic solvent is combined with an oral drug component with a low water solubility to increase surface area, thereby decreasing dissolution time. Alternatively, a dissolving solvent is combined with an oral drug component to cause the oral drug component to be incorporated into the structural web of the edible structure (170), thereby increasing the time needed for dissolution of the oral drug component.

Figure 5:
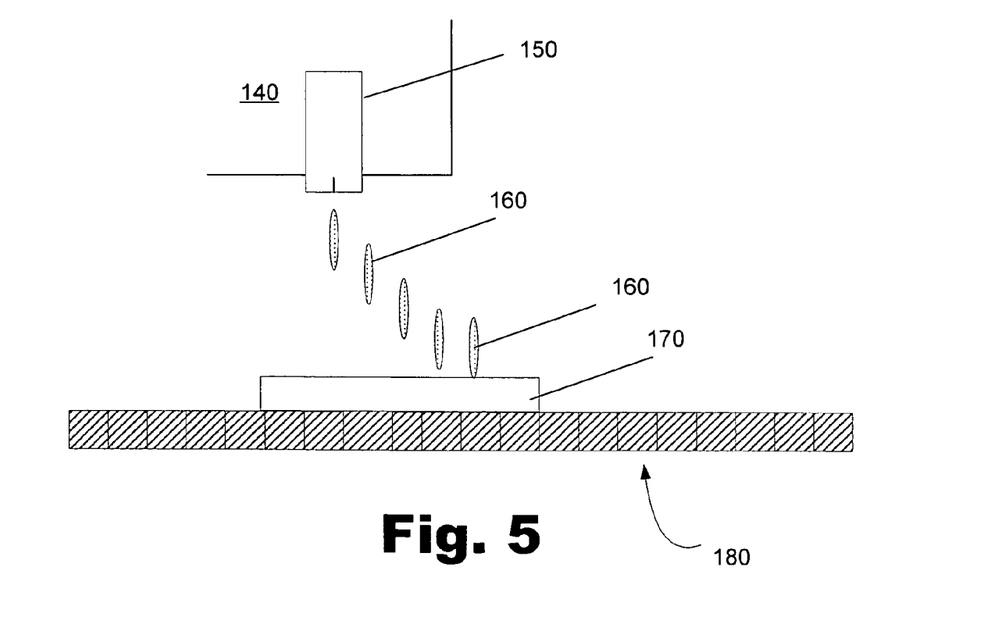
FIG. 5 is a magnified view of the deposition of a jettable pharmaceutical solution onto an edible structure, according to one exemplary embodiment.

Once the jettable pharmaceutical solution has been selected and formulated (step 320; FIG. 3), the jettable pharmaceutical solution may be jetted from the inkjet material dispenser (150) onto the edible structure (170) as illustrated in FIG. 5. As illustrated in FIG. 5, an oral dosage (200) can be prepared in situ by selectively dispensing the jettable pharmaceutical solution (160) from an inkjet material dispenser (150) onto specified and addressable locations of the surface of the edible structure (170).

Figure 6:
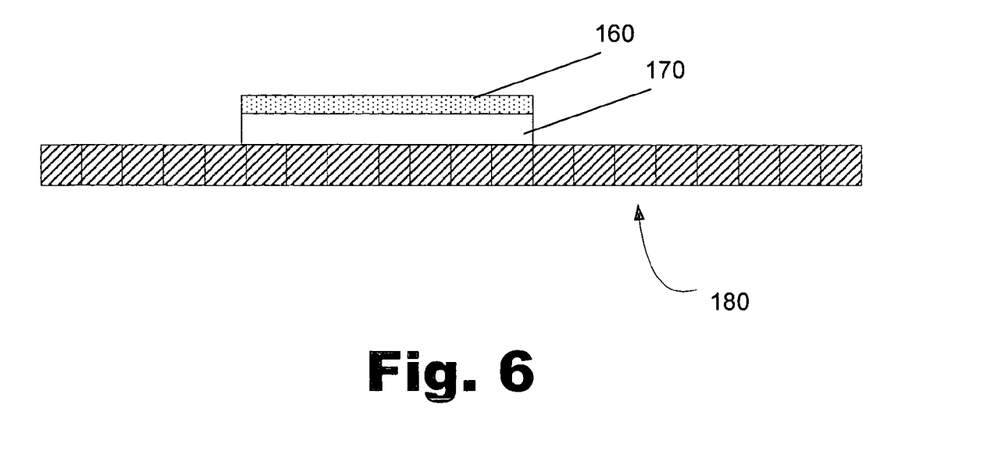
FIG. 6 is a magnified side view illustrating receipt of a jettable pharmaceutical solution onto a pharmaceutical receiving edible structure, according to one exemplary embodiment.

According to one exemplary embodiment illustrated in FIG. 6, a jettable pharmaceutical solution (160) including a solvent that will not dissolve an edible structure (170) will be disposed onto and remain at the surface of the edible structure. As mentioned previously, this exemplary embodiment is advantageous for jettable pharmaceutical solutions (160) containing a low-water soluble oral drug component. By allowing the jettable pharmaceutical solution (160) to remain on the surface of the edible structure (170), a large surface area of the jettable pharmaceutical solution (160) will be exposed resulting in an increased rate of dissolution when consumed.

Figure 7:
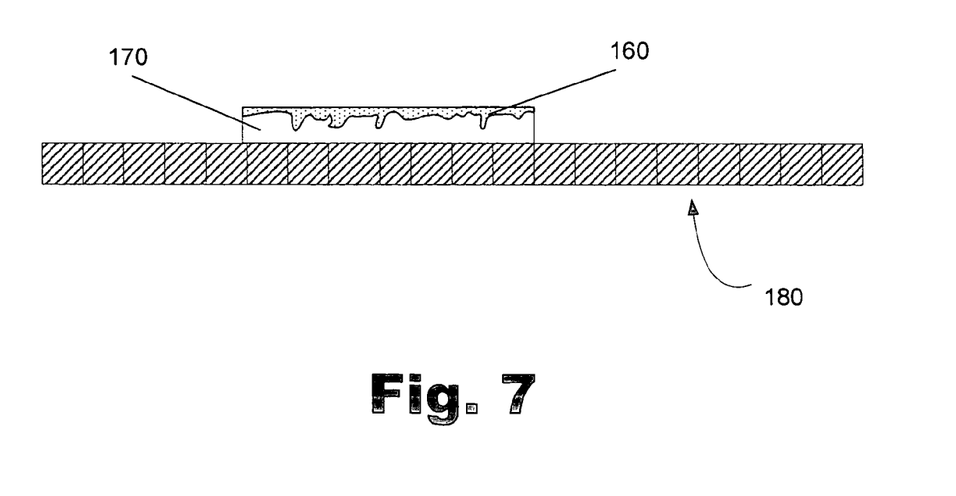
FIG. 7 is a magnified side view illustrating receipt of a jettable pharmaceutical solution onto a pharmaceutical receiving edible structure, according to one exemplary embodiment.

Alternatively, as illustrated in FIG. 7, the jettable pharmaceutical solution (160) may contain a solvent that will slightly dissolve the edible structure (170). According to this exemplary embodiment, the jetted pharmaceutical solution (160) partially dissolves the surface of the edible structure (170). As the edible structure is dissolved, the solvent evaporates leaving the oral drug component in the structural web of the edible structure (170). The exposed surface area, and consequently the release rate of the oral drug component, may vary depending on the solvent component incorporated into the jetted pharmaceutical solution (160).

Once the jettable pharmaceutical has been dispensed onto the surface of the edible structure (step 330; FIG. 3), the formulation system (100; FIG. 1) determines whether the oral dosage formulation operation is complete (step 340; FIG. 3). The formulation system (100; FIG. 1) may determine completion of the oral dosage formulation operation according to any number of methods. According to one exemplary embodiment, the formulation system (100; FIG. 1) may include a flow sensor that determines the amount of jettable pharmaceutical material that is dispensed from the inkjet material dispenser (150; FIG. 1). Once the amount of dispensed pharmaceutical material meets a desired quantity, the formulation system (100; FIG. 1) will indicate a completion of the oral dosage formulation operation. Alternatively, completion of the oral dosage formulation operation may be determined by the computing device evaluating the servo commands communicated to the servo mechanisms.

Returning again to FIG. 3, if the formulation system (100; FIG. 1) determines that the oral dosage formulation operation is not yet complete (NO, step 340), another layer of polymer/gelatin solution (400) may be emitted from the inkjet material dispenser (step 300) and the above method may be performed again until the desired dosage and properties are achieved.

Figure 8:
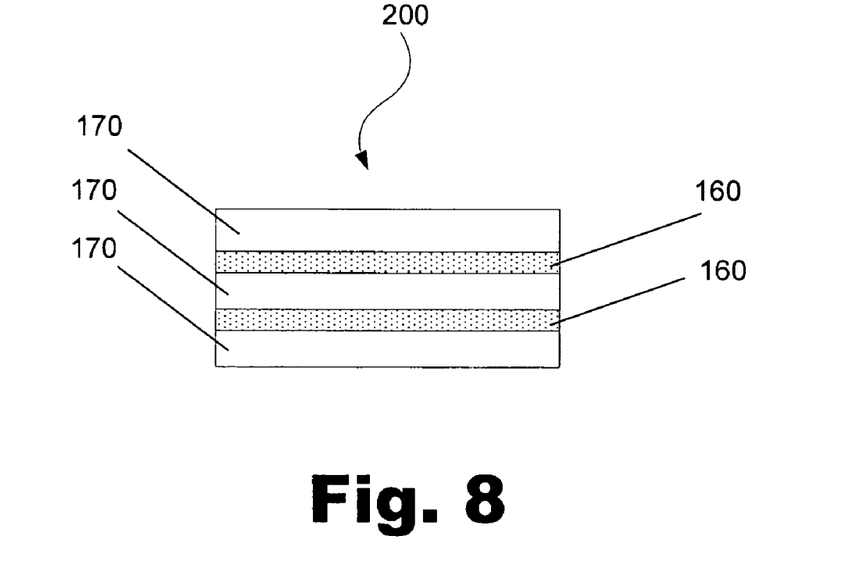
FIG. 8 is a magnified side view of a layered polymer oral dosage according to one exemplary embodiment.
Figure 9:
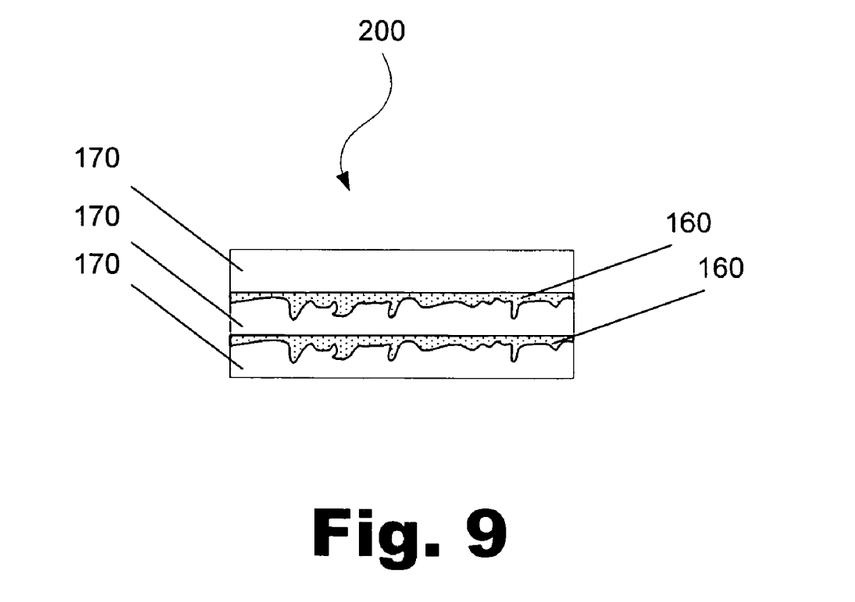
FIG. 9 is a magnified side view of a layered polymer oral dosage according to one exemplary embodiment.

Once the formulation system (100; FIG. 1) determines that the oral dosage formulation operation is complete (YES, step 340) and the desired layered oral dosage (200; FIG. 2) has been formed, the resulting layered oral dosage may be removed from the substrate (180; FIG. 1). FIGS. 8 and 9 illustrate exemplary oral dosages (200; FIG. 2) that have been removed from the substrate. FIG. 8 illustrates a layered oral dosage (200) that was produced with a jettable pharmaceutical solution containing a solvent that does not readily dissolve the edible structure (170). As illustrated in FIG. 8, the resulting jetted pharmaceutical is not intertwined with the structural web of the edible structure (170). Consequently, when consumed, the layered oral dosage (200) is readily dissolved.

In contrast to the configuration illustrated in FIG. 8, the layered oral dosage (200) illustrated in FIG. 9 was formed with a jettable pharmaceutical solution that contained a solvent which partially dissolves the edible structure (170). Consequently, the jettable pharmaceutical solution (160) illustrated in FIG. 9 will have a delayed time of dissolution which may be designed to produce a specific desired dosage and/or release characteristic. Additionally, a plurality of edible structure layers (170) may be formed to further retard the dissolution of the layered oral dosage (200).

In conclusion, the present system and method for producing layered polymer or gelatin oral dosage forms decreases the design constraints inherent in forming oral medication dosages. More specifically, by using the polymer or gelatin edible structures to receive and support the jetted pharmaceutical solution, the amount of excipients used may be minimized. Additionally, variations of the solvent used in the jettable pharmaceutical solution may vary the temporal drug release characteristics of the resulting layered solid dosage form. Moreover, the present system and method increase uniformity of dosage across the layered oral dosage due to the volume control of the inkjet material dispenser, allow for in situ dosage form preparation, allow for the customization of the drug release profile, and may incorporate water soluble as well as insoluble pharmaceutical products.

The preceding description has been presented only to illustrate and describe exemplary embodiments of the present system and method. It is not intended to be exhaustive or to limit the system and method to any precise form disclosed. Many modifications and variations are possible in light of the above teaching. It is intended that the scope of the system and method be defined by the following claims.

What is claimed is:

1. A method for producing an oral medication comprising:
   with an inkjet dispenser mounted on a movable carriage, dispensing a structural material, said structural material including one of a polymer or a gelatin:
   curing said structural material;
   with a second inkjet dispenser mounted on said movable carriage, dispensing a jettable pharmaceutical solution onto said cured structural material; and dispensing alternating layers of said structural material and said pharmaceutical solution.

2. The method of claim 1, wherein said inkjet dispenser comprises one of a thermally actuated inkjet dispenser, a mechanically actuated inkjet dispenser, an electro-statically actuated inkjet dispenser, a magnetically actuated dispenser, a piezo-electrically actuated inkjet dispenser, or a continuous inkjet dispenser.

3. The method of claim 1, wherein said dispensing said structural material comprises:
   selectively jetting said structural material from said inkjet dispenser;

said inkjet dispenser comprising one of a thermally actuated inkjet dispenser, a mechanically actuated inkjet dispenser, an electro-statically actuated inkjet dispenser, a magnetically actuated dispenser, a piezo-electrically actuated inkjet dispenser, or a continuous inkjet dispenser.

4. The method of claim 1, wherein said step of curing said structural material comprises vacuum drying or thermally drying said structural material.

5. The method of claim 1, further comprising curing said alternating layers of said structural material prior to dispensing said alternating layers of said pharmaceutical solution.

6. The method of claim 1, wherein said structural material comprises one of a maltotriose-based pullulan, a gelatin, a polyvinyl alcohol (PVA), a PVA-polyethylene oxide, a PVA-vinylamine, a polyvinyl pyrrolidone (PVP), a PVP-polyvinyl acetate, a cationic PVP, a crosslinked PVP, a sorbitol, a wheat gluten, a seaweed, a cellulose, a methyl cellulose, a hydroxypropyl methyl cellulose (HPMC), a poly vinyl methyl ether (PVME), a PVME-propylene glycol monomethyl ether acetate (PMA), a poly (2-ethyl 2-oxazoline), or a pectin.

7. The method of claim 1, wherein said dispensing a structural material further comprises dispensing a plurality of selective quantities of said structural material onto discrete locations of a substrate.

8. The method of claim 1, further comprising forming said jettable pharmaceutical solution.

9. The method of claim 8, wherein forming a jettable pharmaceutical solution comprises:
presenting an oral drug component; and
combining an edible jettable vehicle component with said oral drug component.

10. The method of claim 9, wherein said oral drug component comprises one of an ace inhibitor, an antianxiety medication, an antibiotic, a antihypertensive medication, an antiviral medication, a blood glucose regulator, an Alzheimer-type dementia medication, an anorexiant, a central nervous system stimulant, an antidiuretic, an antidote, an antihistamine, an antipsychotic medication, an antimanic medication, a beta blocker, a calcium channel blocker, a contraceptive, a dermatologic, a diuretic, an estrogen, a progestin, an entrapyramidal movement disorder medication, a sedative, or a hypnotic medication.

11. The method of claim 10, wherein said oral drug component further comprises one of triazolam, felodipine, trandolapril, pergolide, rivastigmine tartrate, sibutramine hydrochloride, desmopressin acetate, flumazenil, desloratadine, risperidone, carvedilol, isradipine, norgestimate, methoxsalen, metolazone, estradiol, estrogens, conjugated estrogent, esterified cabergoline, zaleplon, or zolpidem tartrate.

12. The method of claim 9, wherein said jettable vehicle component comprises a solvent.

13. The method of claim 12, wherein said solvent is configured to dissolve said oral drug component.

14. The method of claim 13, wherein said solvent is configured to partially dissolve said structural material.

15. The method of claim 14, wherein said solvent comprises one of a water and methanol acetonitrile solvent, an acetone and dimethylsulfoxide (DMSO) solvent, a DMSO and methanol solvent, a DMSO and potassium chloride (KCl) and water solvent, a KCl and water solvent, water, a t-butanol and water solvent, an ethanol and water solvent, a methanol and water solvent, an I-propanol and water solvent, an n-propanol and water solvent, an NaCl and water solvent, a piperazine solvent, a diethylene-diamine solvent, a formamide solvent, a dimethylformamide (DMF), a DMSO solvent, a hexamethylphosphoric triamide solvent, a glycols solvent, a glycerol solvent, a dichloromethane solvent, a polar solvent, an acetone/water solvent, a dioxane solvent, an aqueous alkali solvent, a methanol/methylene chloride solvent, an N-ethylpyridinium chloride and DMF solvent, a chloroform solvent, an acetone solvent, a pyridine solvent, an ester solvent, a cyclohexanone solvent, an N-ethylpyridinium chloride and pyridine solvent, a diluted acid solvent, or an ethylene diamine solvent.

16. The method of claim 13, wherein said solvent is configured to not dissolve said structural material.

17. The method of claim 16, wherein said solvent comprises one of an organic solvent, a hydrocarbon solvent, a chlorinated hydrocarbon solvent, a lower alcohol solvent, a tetrahydrofuran solvent, a ketone solvent, a carboxylic acid solvent, an ester solvent, salt solvent, a water solvent, a diethyl ether solvent, a methylene chloride solvent, an ethanol solvent, an aliphatic hydrocarbon solvent, a diluted aqueous alkali solvent, or an alcohol solvent.

18. The method of claim 12, wherein said jettable vehicle component further comprises one of a humectant, a surfactant, a colorant, a drier, a thinner, a wax, a lubricant, a reducing oil, a solvent, a body gum, a binding varnish, an antioxidant, an anti-skinning agent, a resin, or a binder.

19. The method of claim 1, wherein said dispensing alternating layers of said structural material and said pharmaceutical solution is configured to control a release rate of said pharmaceutical solution.

20. The method of claim 1, wherein said pharmaceutical solution comprises a solvent that dissolves said pharmaceutical solution into said structural material, said method further comprising controlling a quantity of said solvent to control release characteristics of said pharmaceutical solution.

21. The method of claim 1, wherein said pharmaceutical solution comprises a solvent that dissolves said pharmaceutical solution into said structural material, said method further comprising varying said solvent to control release characteristics of said pharmaceutical solution.

22. The method of claim 1, wherein dispensing said structural material comprises depositing a first layer of structural material onto a non-adhesive substrate.

23. The method of claim 22, wherein said non-adhesive substrate comprises glass or polytetrafluorethylene.

24. The method of claim 1, wherein dispensing said structural material comprises depositing a first layer of structural material onto an edible substrate.

25. The method of claim 24, wherein said edible substrate comprises a sheet of edible polymer.

26. The method of claim 25, wherein said edible polymer comprises pullulan, polyvinyl alcohol (PVA), polyvinyl pyrrolidone (PVP), calcium alginate, gelatin, or a combination thereof.

27. The method of claim 1, further comprising controlling said inkjet dispenser and second inkjet dispenser with a computing device to selectively deposit both said structural material and pharmaceutical solution.

28. A method for forming a slow release dosage of oral medication comprising:
disposing a first layer of polymer based structural material adjacent to an inkjet dispenser;
jetting a jettable pharmaceutical solution onto said polymer based structural material with said inkjet dispenser, wherein said solution comprises a solvent for dissolving said solution into said structural material; and
depositing a second layer of polymer based structural material over said pharmaceutical solution; and varying a quantity of said first and second layer of polymer based structural material to vary a release rate of said pharmaceutical solution.

29. The method of claim 28, wherein said inkjet dispenser comprises one of a thermally actuated inkjet dispenser, a mechanically actuated inkjet dispenser, an electro-statically actuated inkjet dispenser, a magnetically actuated dispenser, a piezo-electrically actuated inkjet dispenser, or a continuous inkjet dispenser.

30. The method of claim 28, wherein said polymer based structural material comprises one of a maltotriose-based pullulan, a gelatin, a polyvinyl alcohol (PVA), a PVA-polyethylene oxide, a PVA-vinylamine, a polyvinyl pyrrolidone (PVP), a PVP-polyvinyl acetate, a cationic PVP, a crosslinked PVP, a sorbitol, a wheat gluten, a seaweed, a cellulose, a methyl cellulose, a hydroxypropyl methyl cellulose (HPMC), a poly vinyl methyl ether (PVME), a PVME-propylene glycol monomethyl ether acetate (PMA), a poly (2-ethyl 2-oxazoline), or a pectin.

31. The method of claim 28, wherein said jettable pharmaceutical solution comprises:
an oral drug component; and
an edible jettable vehicle component combined with said oral drug component.

32. The method of claim 31, wherein said solvent is configured to dissolve said oral drug component.

33. The method of claim 28, wherein said solvent comprises one of a water and methanol acetonitrile solvent, an acetone and dimethylsulfoxide (DMSO) solvent, a DMSO and methanol solvent, a DMSO and potassium chloride (KCl) and water solvent, a KCl and water solvent, water, a t-butanol and water solvent, an ethanol and water solvent, a methanol and water solvent, an I-propanol and water solvent, an n-propanol and water solvent, an NaCl and water solvent, a piperazine solvent, a diethylene-diamine solvent, a formamide solvent, a dimethylformamide (DMF), a DMSO solvent, a hexamethylphosphoric triamide solvent, a glycols solvent, a glycerol solvent, a dichloromethane solvent, a polar solvent, an acetone/water solvent, a dioxane solvent, an aqueous alkali solvent, a methanol/methylene chloride solvent, an N-ethylpyridinium chloride and DMF solvent, a chloroform solvent, an acetone solvent, a pyridine solvent, an ester solvent, a cyclohexanone solvent, an N-ethylpyridinium chloride and pyridine solvent, a diluted acid solvent, or an ethylene diamine solvent.

34. The method of claim 28, further comprising dispensing a second layer of polymer based structural material over said jettable pharmaceutical solution.

35. The method of claim 28, further comprising controlling a quantity of said solvent to control release characteristics of said pharmaceutical solution.

36. The method of claim 28, further comprising varying said solvent to control release characteristics of said pharmaceutical solution.

37. The method of claim 28, further comprising adding a surfactant or emulsifier to said solvent.

38. The method of claim 28, further comprising adding a humectant to said solvent.

39. The method of claim 28, further comprising heating said inkjet dispenser.

40. The method of claim 28, wherein disposing said first layer of structural material comprises depositing said first layer of structural material onto a non-adhesive substrate.

41. The method of claim 40, wherein said non-adhesive substrate comprises glass or polytetrafluorethylene.

42. The method of claim 28, wherein disposing said first layer of structural material comprises depositing said first layer of structural material onto an edible substrate.

43. The method of claim 42, wherein said edible substrate comprises a sheet of edible polymer.

44. The method of claim 43, wherein said edible polymer comprises pullulan, polyvinyl alcohol (PVA), polyvinyl pyrrolidone (PVP), calcium alginate, gelatin, or a combination thereof.

45. The method of claim 28, further comprising depositing a plurality of stacked, alternating layers of said structural material and said pharmaceutical solution.

* * * * *

UNITED STATES PATENT AND TRADEMARK OFFICE
CERTIFICATE OF CORRECTION

| | |
|---|---|
| PATENT NO. | : 7,727,576 B2 |
| APPLICATION NO. | : 10/825870 |
| DATED | : June 1, 2010 |
| INVENTOR(S) | : Iddys D. Figueroa et al. |

It is certified that error appears in the above-identified patent and that said Letters Patent is hereby corrected as shown below:

In column 10, line 50, in Claim 1, delete "gelatin:" and insert -- gelatin; --, therefor.

Signed and Sealed this

Fifth Day of October, 2010

David J. Kappos
*Director of the United States Patent and Trademark Office*